United States Patent [19]

Chiarino et al.

[11] Patent Number: 4,772,719

[45] Date of Patent: Sep. 20, 1988

[54] PROCESS FOR THE PREPARATION OF 3,5-DISUBSTITUTED ISOXAZOLES

[75] Inventors: Dario Chiarino; Alberto Sala, both of Monza; Mauro Napoletano, Milan, all of Italy

[73] Assignee: Zambon S.p.A., Vicenza, Italy

[21] Appl. No.: 900,147

[22] PCT Filed: Dec. 10, 1985

[86] PCT No.: PCT/EP85/00693
§ 371 Date: Jul. 24, 1986
§ 102(e) Date: Jul. 24, 1986

[87] PCT Pub. No.: WO86/03490
PCT Pub. Date: Jun. 19, 1986

[30] Foreign Application Priority Data

Dec. 13, 1984 [IT] Italy ................. 24023 A/84

[51] Int. Cl.$^4$ ............................. C07D 261/10
[52] U.S. Cl. .................... 548/247; 548/125; 548/248
[58] Field of Search ............ 548/247, 240, 248

[56] References Cited

PUBLICATIONS

Christoph Grundmann et al., J. Org. Chem., 30(8); pp. 2809–2812 (1965).
Chemical Abstracts, 56, 12869e (1962).

*Primary Examiner*—Donald G. Daus
*Assistant Examiner*—E. Bernhardt
*Attorney, Agent, or Firm*—Stevens, Davis, Miller & Mosher

[57] ABSTRACT

A novel process for the preparation of 3-bromo- and 3-chloro-5-substituted isoxazoles is provided. Dibromo- or dichloro-formaldoxime is reacted with an excess of an 1-alkyne derivative of the formula $$R-C\equiv CH$$

where R is hydrogen, phenyl or 1–6 C alkyl optionally substituted by halogen, OH, OR′, CHO, COR′, COOR′, CONH$_2$, CONR′R″ or NHCOR′ where, in turn, R′ and R″, which may be the same or different, are a 1–6 C alkyl or haloalkyl, in the presence of (i) at least an equimolecular amount, with respect to the dibromo- or dichloro-formaldoxime, of an alkaline base selected from the class consisting of sodium and potassium carbonate and bicarbonate and (ii) an inert solvent in which the 1-alkyne is soluble at room temperature.

3 Claims, No Drawings

PROCESS FOR THE PREPARATION OF 3,5-DISUBSTITUTED ISOXAZOLES

This invention relates to a process for the preparation of 3,5-disubstituted isoxazoles and more specifically of 5-substituted 3-haloisoxazoles.

The process of this invention comprises the reaction of a dihaloformaldoxime with an excess of an 1-alkyne derivative in the presence of an alkaline base in an inert solvent.

The cycloaddition of a dihaloformaldoxime with an alkyne has precedents in the literature (Gazz. Chim. Ital. 91, 47 (1967) and 99, 1107 (1969)). In accordance with this procedure the alkyne is used as organomagnesium derivative.

This fact does limit its applicability only to the alkynes which do not contain functional groups reactive to Grignard compounds.

This procedure cannot be used on industrial scale because of the well-known difficulties in processing and handling the Grignard compounds.

3,5-Disubstituted-isoxazoles, but not 3-halo, 3-hydroxy or 3-alkoxy-5-substituted isoxazoles, may be prepared by cycloaddition according to C. Grundmann, P. Grünanger "The nitrile-oxides" Springer-Verlag, Berlin (1971).

Cycloadditions of dihaloformaldoximes with alkenes to obtain the corresponding 5-substituted 3-halo-isoxazolines are known (Tetrahedron Letters, 21, 229, (1980); 23, 4563, (1982) and 25, 478 (1984)). However, this reaction was specifically studied for the preparation of alpha-amino-3-chloro-4,5-dihydro-5-isoxazolylacetic acid and its 3-bromo analog, these compounds being antitumor agents known as Acivicin and Bromo-acivicin, respectively.

This cycloaddition is carried out by reaction of an excess of dihaloformaldoxime (3–5 times) with the alkene in the presence of a base or of silver nitrate.

Disappointing results were obtained when the procedure was used to condensate a dihaloformaldoxime with an 1-alkyne derivative. The main reaction product was a dihalofuroxan resulting from the reaction between two molecules of dihaloformaldoxime.

The presence of relevant amounts of furoxan is a serious drawback and must be avoided as much as possible because of its dangerousness (J. Chem. Soc. Perkin Trans. I; 294 (1983)) and of problems connected with the isolation of the desired isoxazole derivative.

We have now surprisingly found that 3-halo-isoxazoles having a wide range of substituents at 5-position can be easily prepared with high selectivity and with high yields by reacting a dihaloformaldoxime with an excess (from 2 to 5 times) of an 1-alkyne derivative in the presence of an alkaline base in an inert solvent at room temperature. The formation of furoxans is minimized (see Example 6).

The dihaloformaldoximes which are useful in the process of the present invention are dichloroformaldoxime and dibromoformaldoxime.

The high versatility of the process of this invention is due to the fact that a variety of 1-alkyne derivatives can be successfully used to afford 3-chloro or 3-bromoisoxazoles having at 5-position various different groups.

Suitable 1-alkyne derivative comprise hydrocarbons such as propyne, 1-butyne, 1-pentyne, 1-hexyne, 3-methyl-1-butyne and acetylene; aryl-derivatives optionally substituted at the aromatic ring such as phenylacetylene, 4-chloro phenylacetylene, 4-methylphenylacetylene, 2,4-dimethylphenylacetylene, and the like; compounds containing a hydroxy group such as 3-butyn-2-ol, 3-butyn-1-ol, propargyl alcohol, 1,1-dimethylpropargyl alcohol, 1-pentyn-3-ol, 1-hexyn-3-ol, 1-phenylpropargyl alcohol and the corresponding derivatives in which the hydroxy group is protected such as in the form of tetrahydropyranyl or acyl derivatives; compounds containing an optionally protected carbonyl group like acetal or thioacetal, such as for example propargyl aldehyde, methyl ethynyl ketone, methyl propargyl ketone, ethyl ethynyl ketone, propyl ethynyl ketone, phenyl ethynyl ketone; esters like ethyl propiolate or amides of propiolic and 3-butynoic acid; compounds containing a protected amino group such as for example amides of propargylamine, alpha-methylpropargylamine, alpha,alpha-dimethylpropargylamine, alpha,alpha-diethylpropargylamine, and N-tert.butylpropargylamine; halogenated compounds such as for example propargyl chloride, propargyl bromide, 4-chlorobutyne-1; compounds containing different functional groups such as for example 2-hydroxy-3-butynoic acid esters.

With the process of this invention are prepared 3-chloro or 3-bromoisoxazoles having at 5-position a large number of substituents such as alkyl, aryl, hydroxyalkyl, alkylcarbonyl, alkylcarbonylalkyl, formyl, alkoxycarbonyl, alkoxycarbonylalkyl, aminoalkyl, mono- or dialkylaminoalkyl, haloalkyl, and the like, wherein each alkyl or alkoxy group has from 1 to 6 carbon atoms.

In accordance with the preferred embodiment of this invention dibromo- or dichloroformaldoxime is reacted with an 1-alkyne derivative of formula R—C≡CH wherein R is hydrogen, phenyl or 1–6C alkyl optionally subtituted by halogen, OH, OR′, CHO, COR′, COOR′, CONH$_2$, CONR′R″, NHCOR′ where in turn R′ and R″, the same or different, are an 1–6C alkyl or haloalkyl, to afford 3-bromo- or 3-chloro-5-substituted isoxazoles.

When desired, it is possible to transform these substituents by conventional procedures. Thus, for example, it is possible to substitute the 3-bromo or 3-chloro atom with an alkoxy or arylalkoxy group by reaction with aqeous KOH and the corresponding alcohol. Said group may then be converted into hydroxy and this may be alkylated with alkylanting agents containing different functional groups; examples of such alkylating agents are the chlorohydrins, bromohydrins, epichlorohydrins, and aminoalkyl halides.

Similarly the hydroxy of a hydroxyalkyl group at 5-position may be converted into the corresponding acyloxy, tosyloxy, mesyloxy or haloderivative and these may be substituted with nucleophilic groups such as amines, alcohols, and the like.

The same hydroxyalkyl group may be oxidated to carbonyl or carboxyl group.

The carbonyl of an alkylcarbonyl, alkylcarbonylalkyl or formyl group may be reduced to alcohol or converted into a carbonyl derivative such as hydrazone or oxime.

Hydrolysis of isoxazoles bearing an alkoxycarbonylalkyl group at 5-position affords the corresponding carboxylic acids from which various derivative such as acyl halides, amides and salts or other esters may be prepared by conventional procedures.

The 3,5-disubstituted isoxazoles which can be prepared by the process of this invention may be used in various fields and may also be useful as intermediates for the preparation of other compounds.

Thus for example, 3-chloro- and 3-bromoisoxazoles having at 5-position an optionally substituted phenyl group are endowed with anthelmintic activity (J. Med. Chem., 20, 934, (1977)) or nematocidal activity (U.S. Pat. No. 3,879,532). They can be readily prepared according to the process of this invention by reaction of dichloro- or dibromoformaldoxime with phenylacetylene optionally substituted at the phenyl ring.

Replacement of the bromine or the chlorine atom at 3-position with a hydroxy group gives 3-hydroxy-5-phenylisoxazoles also having anthelmintic activity (J. Med. Chem. 20, 934, (1977)) or antimicrobic activity (Japanese patent application No. 57/165305 (C.A., 99, 34520d)). Said compounds are useful also as intermediates for preparing herbicides (Japanese patent application No. 79/52074 (C.A., 92, 41921u)) or compounds having antiinflammatory activity (Japanese patent application No. 79/73774 (C.A. 92, 41922v) and No. 79/73772 (C.A., 91, 21140y)).

Reaction of dichloro- or dibromoformaldoxime with 1-propyne gives 3-chloro or 3-bromo-5-methylisoxazole which can be easily converted into 3-hydroxy-5-methylisoxazole, a compound endowed with fungicide and phytoregulating activity known as Hymexazol.

In a similar manner it is possible to prepare 3-hydroxy-5-alkylisoxazoles, intermediates for the preparation of compounds having antiinflammatory activity (Japanese patent application No. 79/73772 (C.A., 91, 21140y)).

Reaction of dibromoformaldoxime with 3-butyn-2-ol gives 3-bromo-5-(1-hydroxyethyl)-isoxazole which is converted by oxidation into 3-bromo-5-acetylisoxazole, an intermediate for the preparation of 1-(3-bromoisoxazol-5-yl)-2-tert.butylamine-ethanol, a compound having broncodilating activity (European Patent No. 16255) known as Broxaterol.

In a similar manner it is possible to prepare 5-acetylisoxazoles substituted at 3-position with a chlorine atom, a hydroxy, or an alkoxy group. These are intermediates for the preparation of compounds having antiallergic activity described in patent applications No. PCT/EP85/00380 and 00381 in the name of the same applicant.

Reaction of a dihaloformaldoxime and propargyl alcohol affords a 3-halo-5-hydroxymethylisoxazole which can be easily converted into 3-methoxy-5-hydroxymethylisoxazole, an intermediate for the preparation of 3-hydroxy-5-aminomethylisoxazole, a compound having sedative activity known as Muscimol and described in French Pat. No. 1,427,775.

Muscimol may also be prepared by reacting a dihaloformaldoxime with a protected propargylamine affording a 3-halo-5-aminomethyl-isoxazole which is easily converted into the 3-hydroxy derivative.

Another intermediate for the synthesis of Muscimol is the oxime of the 3-hydroxy-5-isoxazolcarboxaldehyde (Japanese patent application No. 66/07677 (C.A., 67, 11480r)); the aldehyde may be prepared by reacting a dihaloformaldoxime with an acetal of propargyl aldehyde and then by transforming the substituent at 3-position of the isoxazole ring and deprotecting the aldehyde group.

Reaction of dichloro- or dibromoformaldoxime and 3-butyne-1-ol gives 3-chloro- or 3-bromo-5-(2-hydroxyethyl)-isoxazole which by oxidation gives 3-chloro- or 3-bromo-5-isoxazolylacetic acid.

The 5-isoxazolylacetic derivatives are intermediates for the preparation of compounds having antibiotic activity (U.K. patent application No. 2,018,247 (C.A., 93, 26449y), German patent application No. 2,409,949 (C.A., 82, 31341j), U.K. Pat. No. 1,464,377).

Preparation of the above cited compounds and intermediates and of other 3,5-disubstituted isoxazoles may therefore be performed in accordance with the process of the present invention by reacting dichloro- or dibromoformaldoxime with an excess (from 2 to 5 mol) of an 1-alkyne derivative and optionally performing the appropriate transformation of the substituents at 3- or 5-position.

The reaction is carried out in an inert solvent in the presence of a mild alkaline base at room temperature.

Suitable solvents are the solvents in which the 1-alkyne derivative is soluble at room temperature. Examples of such solvents are ethyl acetate, dimethylformamide, ethyl ether, aromatic hydrocarbons, acetonitrile and alcohols.

In any case a small amount of water makes the reaction proceeding easier.

Examples of mild alkaline bases are sodium and potassium carbonate or bicarbonate. An equimolecular amount of base with respect to the dihaloformaldoxime is sufficient even though an excess of base (2–3 times the stoichiometric amount) is preferably used.

The reaction proceeds in high yields and high selectivity also at room temperature.

When desired, for example to increase the reaction rate, the mixture can be heated to 50°–70° C.

In the preferred embodiment the reaction is performed by dissolving the 1-alkyne derivative in the solvent. To the solution a small amount of water (approximately 0.1–1% by volume with respect to the solvent) and the predetermined amount of base are added.

To the obtained mixture, stirred at room temperature, the dihaloformaldoxime is added portionwise.

When the addition is over the mixture is stirred at room temperature monitoring the course of the reaction with conventional techniques (NMR or HPLC).

Generally after 3–24 hours at room temperture the reaction is complete.

The reaction mixture is worked up according to conventional procedures in order to eliminate the excess of 1-alkyne derivative, and isolate the isoxazole compound.

The latter product is generally obtained with yields higher than 75% with respect to the dihaloformaldoxime and in some case with substantially quantitative yields.

There may be present in the product small amounts of the corresponding 3,4-disubstituted isomer which may be easily separated by crystallization or fractional distillation. In any case selectivity toward the 3,5-disubstituted isomer is very high.

The following examples illustrate this invention without however limiting it.

EXAMPLE 1

3-bromo-5-(1-hydroxyethyl)-isoxazole

To a stirred mixture of 3-butyn-2-ol (17.5 g; 0.25 mol) and potassium bicarbonate (15 g; 0.15 mol) in ethyl acetate (200 ml) and water (2 ml) at room temperature dibromoformaldoxime (10.14 g; 0.05 mol) is added portionwise.

When the addition is complete (about 3 hours), the mixture is stirred at room temperature for 18 hours and then poured into water until the solid is completely dissolved.

The organic layer is separated, washed with water and dried over sodium sulfate.

The solvent is removed by evaporation at reduced pressure. The residue (9.6 g) is distilled, collecting the fraction boiling at 90° C. at 0.4 mmHg (colourless oil, 8.55 g; Yield, 89%).

$^1$H-NMR (CDCl$_3$, TMS).

delta (ppm)=6.40 (s, H isoxazole); 5.0 (q, C$\underline{H}$—CH$_3$); 1.6 (d, C$\underline{H_3}$—CH).

In a similar manner dibromoformaldoxime is reacted with propargyl alcohol, ethyl propiolate, phenylacetylene, 1-pentyn-3-ol, 1-hexyn-1-ol, 3-butyn-1-ol, n-butyl 2-hydroxy-3-butanoate, and dichloroformaldoxime is reacted with 3-butyn-2-ol and propargyl alcohol, to afford the following compounds respectively:

3-bromo-5-hydroxymethylisoxazole
  b.p. 100° C. at 1.2 mmHg.
3-bromo-5-ethoxycarbonylisoxazole
  b.p. 80° C. at 0.5 mmHg.
  $^1$H-NMR (CDCl$_3$, TMS).
  delta (ppm)=7.10 (s, H isoxazole); 4.5 (q, C$\underline{H_2}$—CH$_3$); 1.8 (t, CH$_2$-C$\underline{H_3}$).
3-bromo-5-phenylisoxazole
  m.p. 71°-73° C. (n-hexane).
3-bromo-5-(1-hydroxypropyl)-isoxazole
  b.p. 95° C. at 0.5 mmHg.
  $^1$H-NMR (CDCl$_3$, TMS).
  delta (ppm)=6.40 (s, H isoxazole); 4.80 (t, C$\underline{H}$—CH$_2$); 1.90 (m, C$\underline{H_2}$—CH$_3$); 1.06 (t, CH$_2$—C$\underline{H_3}$).
3-bromo-5-(1-hydroxybutyl)-isoxazole
  b.p. 105° C. at 1 mmHg.
  $^1$H-NMR (CDCl$_3$, TMS).
  delta (ppm)=6.40 (s, $\underline{H}$ isoxazle); 4.90 (t, C$\underline{H}$—CH$_2$); 2.20–0.83 (m, CH-C$_3$H$_7$).
3-bromo-5-(2-hydroxyethyl)-isoxazole
  b.p. 105° C. at 1 mmHg.
  $^1$H-NMR (CDCl$_3$, TMS).
  delta (ppm)=6.36 (s, $\underline{H}$ isoxazole); 3.96 (t, C$\underline{HH_2}$); 3.05 (t, C$\underline{H_2}$).
n-butyl 2-(3-bromo-5-isoxazolyl)-2-hydroxy acetate
  b.p. 170° C. at 0.8 mmHg.
  $^1$H-NMR (CDCl$_3$, TMS).
  delta (ppm)=6.50 (s, $\underline{H}$ isoxazole); 5.36 (d, C$\underline{H}$); 4.30 (t, CHHD 2-O); 2.00–0.70 (m, CH$_2$—C$_3$H$_7$).
3-chloro-5-(1-hydroxyethyl)-isoxazole
  b.p. 95° C. at 1 mmHg.
  1H-NMR (CDCl$_3$, TMS).
  delta (ppm)=6.35 (s, $\underline{H}$ H isoxazole); 5.05 (q, C$\underline{H}$-CH$_3$); 1.57 (d, CH—C$\underline{H_3}$).
3-chloro-5-hydroxymethylisoxazole
  b.p. 100° C. at 1 mmHg

EXAMPLE 2

3-bromo-5-aminomethylisoxazole hydrochloride

To a vigorously stirred mixture of N-dichloroacetylpropargylamine (75.9 g; 0.4572 mol) and potassium bicarbonate (68.65 g; 0.6858 mol) in wet N,N-dimethylformamide (610 ml), the dibromoformaldoxime (46.37 g; 0.2286 mol) is added portionwise at room temperature.

When the addition is complete (approximately 3 hours) the mixture is stirred overnight, evaporated under reduced pressure and poured into water and ethyl acetate. The organic layer is separated and evaporated.

The residue is treated with 48% hydrobromic acid (750 ml) and water (250 ml) and refluxed for 4 hours.

After cooling, water (500 ml) is added and the reaction mixture is extracted with ethyl ether.

The aqueous layer is made basic with potassium carbonate and extracted with ethyl ether. The organic layer is washed with water and dried over sodium sulfate.

The ethereal solution is treated with ethereal hydrochloric acid to give a white solid which is crystallized from ethanol yielding 26.8 g of the desired product; m.p. 170° C. (dec.); overall yield, 73%.

In a similar manner dibromoformaldoxime is reacted with N-dichloroacetyl-2,2-dimethylpropargylamine to afford:

3-bromo-5-(1-methyl-1-amino-ethyl)-isoxazole hydrochloride
  m.p. 164°-166° C. (acetonitrile).
  $^1$H-NMR (DMSO, TMS).
  delta (ppm)=7.16 (s, $\underline{H}$ isoxazole); 1.73 (s, CH$_3$, CH$_3$).

EXAMPLE 3

3-methoxy-5-phenylisoxazole

To a stirred solution of potassium hydroxide (15 g; 0.267 mol) in water (7.5 ml) a solution of 3-bromo-5-phenylisoxazole (5 g; 0.0223 mol) in methanol (42.5 ml) is added and refluxed for 24 hours.

The reaction mixture is evaporated to dryness, the residue is poured into water, and extracted with methylene chloride.

The organic layer is washed with water, dried over sodium sulfate, and evaporated.

The residue is crytallized from n-hexane to give 3 g of the desired product; m.p. 69°-71° C.; yield, 77%.

In a similar manner the following compounds are prepared:

3-methoxy-5-hydroxymethylisoxazole
  b.p. 95° C. at 0.2 mmHg.
3-methoxy-5-aminomethylisoxazole hydrochloride
  m.p. 175°-177° C. (isopropanol).
3-methoxy-5-(1-hydroxyethyl)-isoxazole
  b.p. 110° C. at 0.6 mmHg.
  $^1$H-NMR (CDCl$_3$, TMS).
  delta (ppm)=5.92 (s, $\underline{H}$ isoxazole), 4.93 (q, C$\underline{H}$—CH$_3$); 4.00 (s, OCH$_3$); 1.55 (d, CH—C$\underline{H_3}$).
3-methoxy-5-(1-methyl-1-amino-ethyl)-isoxazole hydrochloride
  170°-172° C. (acetonitrile).
  $^1$H-NMR (DMSO, TMS).
  delta (ppm)=6.49 (s, $\underline{H}$ isoxazole); 3.96 (s, CH$_3$O); 1.70 (s, CH$_3$, CH$_3$).

EXAMPLE 4

3-bromo-5-acetylisoxazole

Into a solution of 3-bromo-5-(1-hydroxyethyl)-isoxazole (24.2 g; 0.126 mol) in glacial acetic acid (190 ml) cooled to 15° C. a solution of chromic anhydride (9.2 g; 0.0924 mol) in glacial acetic acid (135 ml) and water (9.5 ml) is added dropwise.

The reaction mixture is stirred at room temperature for 6 hours.

The solvent is evaporated under reduced pressure, the residue is poured into water, and neutralized with sodium bicarbonate.

The aqueous layer is extracted with ethyl ether. The organic layer is separated, washed with water, dried over sodium sulfate, and evaporated.

The residue (21 g) is crystallized from n-hexane to give 18.1 g of the desired product; white solid; m.p. 65°–66° C.

In a similar manner 3-methoxy-5-(1-hydroxyethyl)-isoxazole, 3-bromo-5-(1-hydroxypropyl)-isoxazole and 3-bromo-5-(1-hydroxybutyl)-isoxazole were oxidized to afford 3-methoxy-5-acetylisoxazole
(b.p. 95° C. at 15 mmHg)

3-bromo-5-propionyl-isoxazole
b.p. 70° C. at 0.5 mmHg; m.p. 35°–37° C.
$^1$H-NMR (CDCl$_3$, TMS).
delta (ppm)=7.02 (s, H isoxazole); 3.03 (q, CH$_2$—CH$_3$); 1.25 (t, CH$_2$—CH$_3$).

3-bromo-5-butirroylisoxazole
b.p. 80° C. at 0.5 mmHg.
$^1$H-NMR (CDCl$_3$, TMS).
delta (ppm)=7.03 (s, H isoxazole); 2.96 (t, CH$_2$—CO); 1.80 (m, CH$_2$—CH$_3$); 1.03 (t, CH$_2$—CH$_3$).

EXAMPLE 5

3-bromo-5-carboxyisoxazole 3-bromo-5-ethoxycarbonylisoxazole (11 g; 0.05 mol) is added to a 5% aqueous solution of sodium hydroxide (110 ml).

The mixture is stirred at room temperature for 1 hour, then acidified with 37% hydrochloric acid and extracted with ethyl acetate. The organic layer is separated, washed with water, dried over sodium sulfate, and evaporated.

The residue is crystallized from chloroform giving 9.0 g of the desired product; white solid, m.p. 176°–177° C.

EXAMPLE 6

HPLC analysis of cycloaddition between dibromoformaldoxime (A) and 3-butyn-2-ol (B)

The reactions are carried on as described in Example 1.

Dibromoformaldoxime (1.014 g; 0.005 mol) is added portionwise to mixtures of variable amounts of 3-butyn-2-ol, potassium bicarbonate (1.5 g; 0.015 mol) in ethyl acetate (20 ml) and water (0.2 ml). After stirring overnight water is added (10 ml) and the organic layers is separated, washed twice with water (2×5 ml) and dried.

Samples of 1 ml of the organic layers are diluted to 20 ml with acetonitrile and submitted to HPLC analysis (Beckman 344 apparatus; eluent, acetonitrile:water 1:1).

The results are reported in the following table.

| Molar ratio (A):(B) | 3-bromo-5-(1-hydroxyethyl) isoxazole (weight %) | dibromofuroxan (weight %) |
| --- | --- | --- |
| 1:5 | 99.8 | 0.2 |
| 1:3 | 98.1 | 1.9 |
| 1:2 | 97.9 | 2.1 |
| 1:1 | 76.5 | 23.5 |
| 2:1 | 63.3 | 36.7 |

We claim:

1. A process for the preparation of 3-bromo- and 3-chloro-5-substituted-isoxazoles, wherein dibromo- or dichloroformaldoxime is reacted with a 2-to-5-fold molar excess of an 1-alkyne compound of the formula

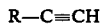

R—C≡CH where R is a hydrogen, phenyl or 1–6 alkyl optionally substituted by halogen, OH, OR′, CHO, COR′, COOR′, CONH$_2$, CONR′R″ or NHCO′, where in turn R′ and R″, which may be the same or different, are a 1–6 C alkyl or haloalkyl, in the presence of (i) at least an equimolecular amount, with respect to the dibromo- or dichloroformaldoxime, of an alkaline base selected from the class consisting of sodium and potassium carbonate and bicarbonate and (ii) an inert solvent in which the 1-alkyne is soluble at room temperature.

2. A process according to claim 1, wherein the solvent contains an amount of water of from 0.1 to 1% by volume with respect to the organic solvent.

3. The process according to claim 1, wherein the reaction is performed at room temperature.

* * * * *